United States Patent
Farrar

(10) Patent No.: US 7,469,474 B2
(45) Date of Patent: Dec. 30, 2008

(54) MANUFACTURING A COMPONENT WITH A NEAR SPHERICAL SURFACE

(75) Inventor: Richard Farrar, North Rigton (GB)

(73) Assignee: DePuy International Limited, Beeston Leeds (GB)

( * ) Notice: Subject to any disclaimer, the term of this patent is extended or adjusted under 35 U.S.C. 154(b) by 522 days.

(21) Appl. No.: 10/501,655

(22) PCT Filed: Jan. 16, 2003

(86) PCT No.: PCT/GB03/00157

§ 371 (c)(1),
(2), (4) Date: Dec. 29, 2004

(87) PCT Pub. No.: WO03/061532

PCT Pub. Date: Jul. 31, 2003

(65) Prior Publication Data

US 2005/0087047 A1    Apr. 28, 2005

(30) Foreign Application Priority Data

Jan. 17, 2002    (GB) .................................. 0200993.4

(51) Int. Cl.
*B21D 53/10* (2006.01)
(52) U.S. Cl. .................. 29/898.048; 29/557; 408/1 R; 409/51; 451/52; 83/13
(58) Field of Classification Search ............ 29/898.048, 29/557, 28; 408/1 R; 409/51, 132, 143, 409/199, 201, 229; 451/51, 52, 61; 623/22.15, 623/22.42, 22.43; 83/13, 54, 331, 329

See application file for complete search history.

(56) References Cited

U.S. PATENT DOCUMENTS 2,187,471 A * 1/1940 Hutchinson .................. 451/52

(Continued)

FOREIGN PATENT DOCUMENTS

FR    2797207    8/2000

(Continued)

*Primary Examiner*—Jermie E Cozart
(74) *Attorney, Agent, or Firm*—Barnes & Thornburg LLP

(57) ABSTRACT

A method of making a component (2) of an orthopaedic joint prosthesis, which has a bearing surface whose shape corresponds approximately to a part of a sphere and is symmetrical about its polar axis, involves use of a cutting tool (6) which has a circular cutting edge (12) and which can be rotated about an axis (8) which is perpendicular to the plane containing the said cutting edge (12). The method involves (a) rotating the component about its polar axis (4) and rotating the cutting tool (6) about its axis (8), with the cutting edge (12) of the cutting tool (6) in contact with the surface of the component (2); (b) moving the cutting tool (i) in a direction parallel to the polar axis (4) of the component (2) while leaving the angle between the axis of the cutting tool (6) and the polar axis of the component (2) unchanged, and (ii) along its axis (8); and (c) repeating step (a). The movements (i) and (ii) of the cutting tool (6) cause the radius of curvature of the bearing surface to change continuously and monotonically as the angle between the radius and the polar axis of the component changes, so that the shape of the bearing surface deviates from that of a true sphere in such a way that discontinuities in the shape of the bearing surface as a result of individual movements are minimised.

12 Claims, 2 Drawing Sheets

U.S. PATENT DOCUMENTS

| | | | |
|---|---|---|---|
| 3,212,405 A | * 10/1965 | Smith | 409/132 |
| 4,245,939 A | 1/1981 | Sear | |
| 5,823,721 A | 10/1998 | Wagenseil | |
| 6,126,695 A | 10/2000 | Semlitsch | |

FOREIGN PATENT DOCUMENTS

| | | |
|---|---|---|
| GB | 2010143 | 6/1979 |
| JP | 09168957 A * | 6/1997 |
| WO | 83/03691 | 10/1983 |
| WO | 95/23566 | 9/1995 |
| WO | WO 97/16138 | 5/1997 |

* cited by examiner

MANUFACTURING A COMPONENT WITH A NEAR SPHERICAL SURFACE

This application is a U.S. national counterpart application of international application serial No. PCT/GB03/00157 filed Jan. 16, 2003 which claims priority to Great Britain Patent Application No. 0200993.4 filed Jan. 17, 2002. The entirety of both of these applications is hereby incorporated by reference.

This invention relates to a method of making a component of an orthopaedic joint prosthesis which has a bearing surface whose shape corresponds approximately to a part of a sphere and is symmetrical about its polar axis. The component can be used in the replacement of diseased or damaged ball and cup joints of the human or animal body.

Implantable joint prostheses for joints such as hip and shoulder joints comprise a rounded head on a stem which can fit into the intramedullary cavity of the long bone, and an implantable cup which can receive the rounded head for articulation of the joint.

Careful preparation of the bearing surfaces of the head and cup components of a joint prosthesis is necessary to obtain satisfactory articulation. The surfaces should have a significant contact area so that the load is spread. However, it is also important to maintain a small clearance between the bearing surfaces for lubricating fluid. Control over the clearance is important to maintain satisfactory lubrication. An incorrect clearance, whether too large or too small, can allow direct contact between the bearing surfaces, leading to wear of the surfaces and the generation of wear debris.

Use of components which have bearing surfaces with spherical geometries requires that the diameter of the head component is slightly smaller than the internal diameter of the cup component, in order that a clearance is maintained between the surfaces. However, this means that the load is transferred between the surfaces only at a point or a small contact area; it is not possible to obtain a true surface-to-surface load bearing relationship when the two surfaces are spherical but with different diameters.

WO-A-97/16138 discloses a joint prosthesis in which the articulating surfaces of the head and cup components have complex configurations. Each bearing surface has a spherical portion at about its pole. The spherical portions are in surface-to-surface load bearing relationship. Each bearing surface has a non-spherical portion where the surfaces diverge, by changing the radius of curvature of the bearing surface of the cup component to a bigger value, and decreasing the radius of curvature of the bearing surface of the head component to a smaller value. The resulting bearing surfaces include line discontinuities at the point where the radii change. This can give rise to increased wear at the regions of these lines where these discontinuities are located.

WO-A-95/23566 discloses a joint prosthesis in which an acetabular cup has a concave bearing socket for receiving the head of a femoral component of a hip prosthesis. The radius of curvature of the surface of the socket continuously and monotonically decreases from the lip of the socket to a minimum value ($R_2$) at a point within the socket. The head of the ball component has a primarily spherical geometry with a radius of curvature of $R_1$, with $R_1$ being less than $R_2$ by a small amount. Away from the actual pole, the surfaces diverge to leave an increasing clearance between the monotonically diverging surfaces. The non-spherical bearing surface of this patent is continuous because the radius varies continuously and in a consistent direction (that is to say, monotonically) but decreases to a point. A problem with this design is that the disclosed bearing surfaces can never provide the load transfer characteristics which are available from two surfaces in surface to surface contact.

An orthopaedic joint prosthesis is disclosed in International patent application no. GB01/05307 in which the bearing surfaces of the mating components are spherical over a part of their area in a polar region (relative to the axis of the component), and in which the surface of at least one of the components deviates from sphericity between that polar region and the equator of the component. This deviation from sphericity need only be small. However, it can mean that the disclosed prosthesis can provide an area of surface to surface contact at the pole of the bearing surface, which allows smooth articulation of the joint while the variation in the radius of curvature of the bearing surface means that likelihood of the joint locking against continued articulation, for example because of imperfections due to limitations on manufacturing techniques, is reduced. Features of an orthopaedic joint component whose shape deviates from sphericity, including features of shape and of techniques for its manufacture, which are disclosed in that document, are applicable to the component of the present invention and are incorporated in the specification of the present application by this reference.

The present invention provides a technique for making orthopaedic joint prostheses with approximately spherical bearing surfaces, which facilitates the manufacture of those surfaces with configurations which deviate from true sphericity, for example as disclosed above.

Accordingly, in one aspect, the invention provides a method of making a component of an orthopaedic joint prosthesis which has a bearing surface whose shape corresponds approximately to a part of a sphere and is symmetrical about its polar axis, the method making use of a cutting stone which has a circular cutting edge and which can be rotated about an axis which is perpendicular to the plane containing the said cutting edge, and comprising the steps of:

a. rotating the component about its polar axis and rotating the cutting tool about its axis, with the cutting edge of the cutting tool in contact with the surface of the component, and b. moving the cutting tool (i) in a direction parallel to the polar axis of the component while leaving the angle between the axis of the cutting tool and the polar axis of the component unchanged, and (ii) along its axis, and c. repeating step (a), the movements (i) and (ii) of the cutting tool causing the radius of curvature of the bearing surface to change continuously and monotonically as the angle between the radius and the polar axis of the component changes, so that the shape of the bearing surface deviates from that of a true sphere in such a way that discontinuities in the shape of the bearing surface as a result of individual movements are minimised.

The method of the present invention is based on conventionally used techniques for making joint components with bearing surfaces which are approximately spherical. These make use of a cutting tool which has a circular cutting edge and which can be rotated about an axis which is perpendicular to the plane containing the said cutting edge. When the component is hollow so that the bearing surface is concave (often referred to as a cup component), the cutting tool can be in the form of a disk and the cutting edge will be the outside edge (or corner) of that disk. When the bearing surface is convex, the cutting tool will have a central hole (for example, it will be annular), and the cutting edge of the tool will be provided by the internal edge of that hole. An annular cutting tool can have circular inner and outer cutting edges so that it can be used to form concave and convex bearing surfaces on respective components. The cutting tool should generally be selected so that the diameter of the cutting edge is at least big enough to engage the component over both the pole of the component (defined by the axis of rotational symmetry) and the equator.

Materials for cutting tools which can be used in the method of the present invention are well known.

The action of pressing the rotating cutting tool against the rotating component allows material to be removed from the surface of the component and inherently leaves the component with an accurately spherical surface. Highly polished surfaces can be obtained by use of cutting tools with progressively finer particle size.

According to the present invention, it has been found that it is possible to control deviations from true sphericity of the bearing surface of a component by movement of the cutting tool relative to the surface of the component. There are two movements of the cutting tool relative to the component (which will generally be movement of the cutting tool itself, but which can be performed by movement of the component) which can be carried out sequentially or simultaneously. One of the movements involves moving the cutting tool in a direction parallel to the polar axis of the component while leaving the angle between the axis of the cutting tool and the polar axis of the component unchanged. This movement will be in a direction away from the bearing surface of the component. The other movement of the cutting tool takes place along its own axis will be in a direction towards the bearing surface when the bearing surface of the component is concave and will increase the radius of the surface with continued movement. The movement of the cutting tool along its axis will also be in a direction towards the bearing surface when the bearing surface of the component is convex and will reduce the radius of the surface with continued movement.

It has been found that the combination of the two movements of the cutting tool can produce a component which is rotationally symmetrical about the axis of the component, and in which the radius of the sphere changes continuously and monotonically as the angle between the radius and the polar axis of the component changes. The two movements of the cutting tool can be made continuously under appropriate control of the tool, for example using motorised drives for the component and the cutting tool which are controlled using appropriate software. However, it has been found that the movements of the cutting tool can be made in steps and that deviations from sphericity which are adequate to achieve the objectives identified in patent documents discussed above can be obtained without unacceptable discontinuities in the bearing surface. This involves ensuring that two movements of the cutting tool are properly matched and performed in conjunction with one another (when they are not performed simultaneously).

Preferably, the portion of the bearing surface which is defined by the cutting tool before it has been moved along the workpiece axis extends through an angle of arc (which will be the half angle of a cone on the polar axis) of at least about 5°, preferably at least about 10°, for example about 15°.

When the cutting tool is moved incrementally, it can be preferred for the portion of the bearing surface which is defined by the cutting tool between any pair of consecutive incremental movements thereof to extend through an angle of arc of at least about 1°, more preferably at least about 3°, for example at least about 7°. Preferably, the said angle of arc is not more than about 20°, more preferably not more than about 10°. The angle of arc is determined by the extent of the movement of the cutting tool in a direction parallel to the polar axis of the component, and the change in the radius of the spherical surface that is created by the cutting tool after the movements (i) and (ii). Relatively large angles of arc give rise to the advantage of reducing the number of cutting operations to be performed on the component. Relatively small movements have the advantage of enabling a component to be produced with minimal discontinuities at each change in actual radius, and also enabling small deviations from sphericity (for example measured in terms of increase in effective radius at the equator) to be obtained. Preferably, the ratio of the distance through which the cutting tool is moved in each incremental step to the radius of the component at the pole is not more than about 0.15, more preferably not more than about 0.10, especially not more than about 0.07, for example not more than about 0.035 or not more than about 0.02.

Generally, the deviation from sphericity of the bearing surface of the component will be small. For example, it can be preferred for the maximum width of the space that is introduced between the bearing surface of the component and the corresponding bearing surface of a mating component to be not more about 1 mm wide, for example not more than about 500 µm, preferably not more than about 300 µm, especially not more than about 100 µm, for example not more than about 60 µm. The width of space will generally be at least about 15 µm, for example from about 20 µm to about 50 µm. The width of the space will generally increase gradually from the circumferential line at which the changes in radius cease in a direction away from the pole of the components. Generally, the width of the space will be at its greatest at or towards the equator of the component. Generally, the deviation from sphericity will only be applied to one of the components while the other component will have a substantially constant radius of curvature over most, or preferably all, of its bearing surface. This has several advantages, including simplification of the manufacture of one of the components.

The width of the space between the components in the region in which the bearing surface has a constant radius of curvature will usually be substantially constant. The space in that region will often be less than about 10 µm, for example less than about 5 µm, and possibly as little as 2 µm or less.

The configuration of the bearing surface of the component can be such that the bearing surface has a spherical portion at the pole. The portion which is remote from the pole can be spherical but with a different radius, for example as disclosed in WO-A-97/16138. The portion which is remote from the pole can have a radius of curvature which then changes continuously and monotonically as the angle between the radius and the polar axis increases, as disclosed in International patent application no. GB01/05307.

The configuration of the bearing surface can be such that the radius decreases continuously and monotonically from the equator of a cup component to a minimum value at a point within the cup, increases continuously and monotonically from the equator of a spherical head component to a maximum value at a point on the head, generally the pole. Such a cup component is disclosed in WO-A-95/23566.

Preferably, the bearing surface of the finished component includes a portion at and around the pole over which the radius of curvature is approximately constant. For example, the portion of the bearing surface over which the radius of curvature is approximately constant extends over a cone half angle of at least about 10°, preferably at least about 15°, more preferably at least about 20°, for example about 30°. The spherical portion around the pole is obtained when the axis of the cutting tool along which it is moved passes through the centre of the sphere of which the polar region of the bearing surface forms a part.

The method of the invention can include a step of sterilising the component so that it is suitable for implantation in a human or animal body as a component of a joint prosthesis.

The material for the component can be selected from materials which are commonly used for orthopaedic joint prosthesis components. Such components are commonly made from materials such as metallic, polymeric and ceramic materials. The present invention is particularly suited to joint prostheses in which mating bearing surfaces are both hard, for example in which mating bearing surfaces are both selected from metallic and ceramic materials. Those bearing surfaces might be the same or different. Suitable metallic materials include cobalt chrome alloys, titanium alloys, and certain stainless steels. Suitable ceramic materials will generally be a dense, hard, crystalline, non-metallic materials, especially inorganic materials. A bearing material might be formed from such a material by a process which includes, for example, exposure to high temperature and pressure. Examples of ceramic materials include hard oxides. Examples of suitable hard oxide materials include aluminium oxide (alumina) and zirconium oxide (zirconia). Zirconium oxide will preferably be used in mixtures with other materials such as one or more of aluminium oxide and yttrium oxide. Other ceramic materials include certain carbides and nitrides, such as carbides and nitrides of titanium, chromium, silicon, aluminium and zirconium.

The component of the invention can be made from more than one material. For example, the component can be made from a first material, with a surface provided by another material. The use of ceramic surfaces for the component can provide advantages in terms of wear resistance.

The component of the present invention has a bearing surface which is rotationally symmetrical, at least over a portion of its surface around the pole. The component need not be rotationally symmetrical. For example, the component might include a lip portion where the extent of the bearing surface relative to the equator is different from the extent of the bearing surface over the remainder of the component The component of the invention might be a part of a hip joint prosthesis or a shoulder joint prosthesis, or as a part of another prosthesis such as a spine component prosthesis. When the component is a femoral component of a hip joint prosthesis or a humeral component of a shoulder joint prosthesis, it can have a convex head. When it is an acetabular component of a hip joint prosthesis, it can have a concave cup.

The bearing surface of the component will be finished so that it is smooth and substantially free of imperfections. Techniques for finishing the surface are known in connection with the manufacture of orthopaedic joint prosthesis components. Preferably, the bearing surface has a roughness of not more than about 0.015 μm $R_a$, more preferably not more than about 0.01 μm $R_a$, especially not more than about 0.008 μm $R_a$, for example not more than about 0.005 μm $R_a$, as measured using conventional surface profilometer apparatus.

Embodiments of the present invention will now be described by way of example with reference to the accompanying drawings, in which.

Figure 1:
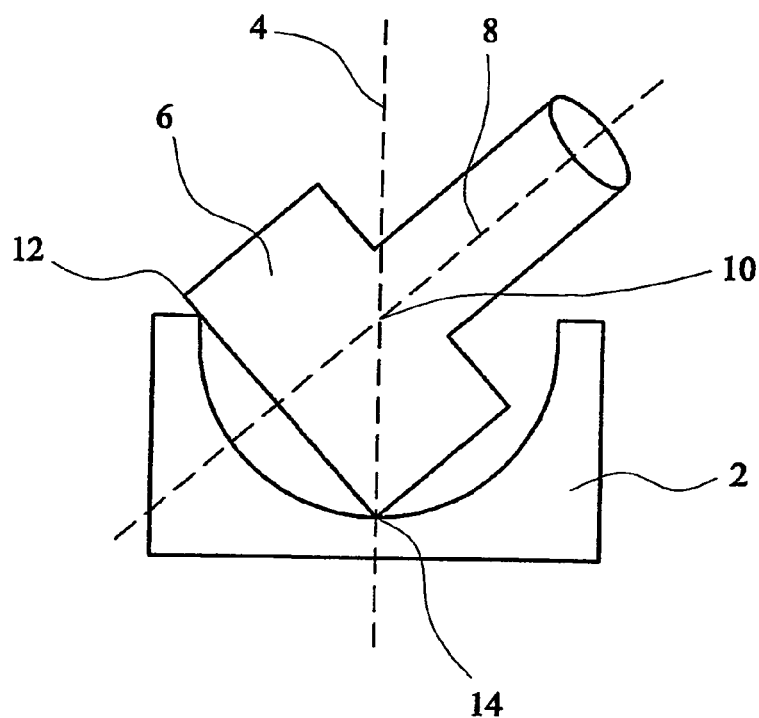
FIG. 1 is a sectional elevation through a schematic representation of apparatus for finishing the spherical bearing surface of a hollow cup component of an orthopaedic joint prosthesis.

Referring to the drawings, FIG. 1 shows a hollow workpiece 2 which has a roughly spherical shape. The workpiece has a poor finish and unacceptable deviations from sphericity, resulting from its manufacture, for example by casting techniques or by rough machining.

It is known to finish the bearing surface of a hollow workpiece using apparatus which enables the workpiece to be rotated about its axis of symmetry 4. A microfinishing stone 6 is fitted to a rotating drive and is made to rotate about its axis 8, arranged so that the axes of the workpiece and the stone intersect at the centre 10 of the sphere defined by the workpiece. The stone is circular and has a diameter which is such that the cutting edge 12 on the circumference of the stone contacts the surface at the pole 14 of the workpiece and overlaps its equator. The action of the circular cutting edge 12 of the stone against the hollow surface of the workpiece 2 results in removal of material from the surface of the workpiece, and leaves the workpiece with a smooth surface with an accurately spherical shape. The finish of the surface can be optimised by use of progressively finer particle size finishing stones. Apparatus of this kind is available from the German company Thielenhaus.

The present invention provides a technique for making a component of an orthopaedic joint prosthesis in which movements of the cutting tool cause the effective radius of curvature of the bearing surface of the component (measured to the centre of the sphere that is defined by the bearing surface at the pole) to change continuously and monotonically as the angle between the radius and the polar axis of the component changes. The movements are shown schematically in FIG. 2.

Figure 2:
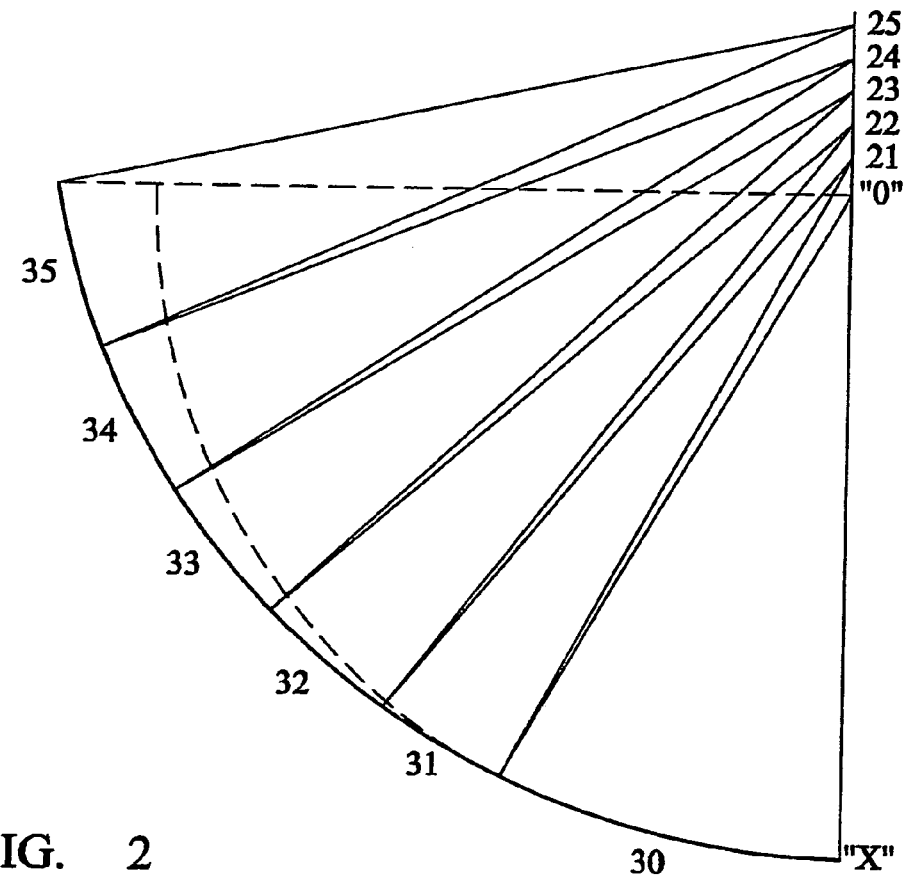
FIG. 2 is a graphical representation showing how a cutting tool can be moved during manufacture of a joint prosthesis component so that the shape of the bearing surface deviates from sphericity.

FIG. 2 shows schematically a half portion of the workpiece 2 shown in FIG. 1, with the axis of the workpiece around which it is rotated extending from the pole "X" through the centre of the sphere "O" (equivalent to the point 10 in FIG. 1). When the axis 8 of the cutting tool 6 extends through the centre "O" of the sphere (as shown in FIG. 1), the workpiece is formed with a spherical shape, as is known.

According to the present invention, the workpiece is formed with a shape which deviates from sphericity in that the radius of curvature of the bearing surface (measured between the centre "O" and the bearing surface) increases continuously as the angle between the radius and the polar axis (X-O) increases. This is achieved by moving the cutting tool along the polar axis in a direction parallel to the polar axis so that the angle between the polar axis and the rotational axis 4, X-O of the cutting tool remains constant. The cutting tool is also moved along its rotational axis 8 after each successive movement along the polar axis (X-O) in a direction towards the workpiece until the cutting tool comes into contact with the bearing surface of the workpiece. As shown in FIG. 2, the cutting tool is moved from the position in which its rotational axis 8 intersects the centre "O" of the sphere to five positions (21 to 25) in which its rotational axis is located progressively further from the centre "O" of the sphere. When the cutting tool is in its first position (with its rotational axis 8 intersects the centre "O" of the sphere), the cutting tool creates a portion 30 of the bearing surface at and around the pole which is spherical. After the first movement of the cutting tool, to the position in which its rotational axis 8 intersects the polar axis of the component at the point 21, the rotation of the workpiece and the cutting tool results in the formation of a surface of a partial sphere whose radius extends from the point 21 on the polar axis. After the second movement of the cutting tool, to the position in which its rotational axis 8 intersects the polar axis of the component at the point 22, the rotation of the workpiece and the cutting tool results in the formation of a surface of a partial sphere whose radius extends from the point 22 on the polar axis. The part of the sphere 31 whose radius extends from the point 21 on the polar axis is then reduced to a collar-like part of the bearing surface. Subsequent movements of the cutting tool produce successive collar-like parts (32 to 35) of the bearing surface of increasing radius.

Provided that the distance between the successive sphere centres "O", 21 to 25 is not too great, it has been found that discontinuities on the bearing surface resulting from each change in the actual radius of the bearing surface are acceptably low.

EXAMPLE

The method of the present invention has been used applied using computer modelling software to show how a hollow cup component can be made. Before the cutting and finishing step, the cup component 2 has a spherical shape with a radius of 14 mm. The bearing surface of such a cup can be finished using conventional techniques using a finishing stone 6 having a radius of 9.9 mm.

The cup component and the cutting tool are each arranged to rotate about their respective axes 4, 8, with the angle between the axes set at 45° (although other angles can be used) and so that the axes intersect at the centre of the sphere defined by the surface of the cup. The cutting tool is moved along its own axis so that its cutting edge is 9.9 mm from the point where the axes of the component and the tool intersect. Action of the cutting tool on the internal surface of the cup component produces a bearing surface 30 which is spherical, with a radius of 14 mm.

When the surface finish of the component is acceptable (at least on the polar region), the cutting tool 6 is withdrawn along its axis. The tool is then translated along the polar axis of the component by 0.5 mm (so that the ratio of the distance through which the cutting tool is moved to the radius of the component at the pole is 0.0357 mm), and is moved along its own axis into contact with the bearing surface. Action of the cutting edges of the tool as it is advanced along its axis removes material from the bearing surface until the front face of the tool (whose edges provide the cutting surfaces of the tool) is 10.5 mm from the point where the axes of the component and the tool intersect. Action of the cutting tool on the internal surface of the cup component produces a bearing surface 31 which is spherical, with a radius of 14.431 mm (measured from the intersection of the axes 4, 8).

The tool is moved four more times, to provide bearing surface parts 32 to 35, as follows:

| Sphere portion (see FIG. 3) | Movement of cutting tool axis (mm) | Tool face to axes intersection (mm) | Radius of sphere portion (mm) |
| --- | --- | --- | --- |
| 30 | 0.0 | 9.9 | 14.000 |
| 31 | 0.5 | 10.5 | 14.431 |
| 32 | 1.0 | 11.0 | 14.798 |
| 33 | 1.5 | 11.4 | 15.099 |
| 34 | 2.0 | 11.7 | 15.330 |
| 35 | 2.5 | 11.87 | 15.455 |

The combined movements of (i) the cutting tool axis and (ii) the cutting tool face along the tool axis are selected to provide angles of arc for the sphere portions of about 30° for the polar portion 30 (so that the cone angle at the pole is 60°), and of about 12° for each of the portions 31 to 35.

Figure 3:
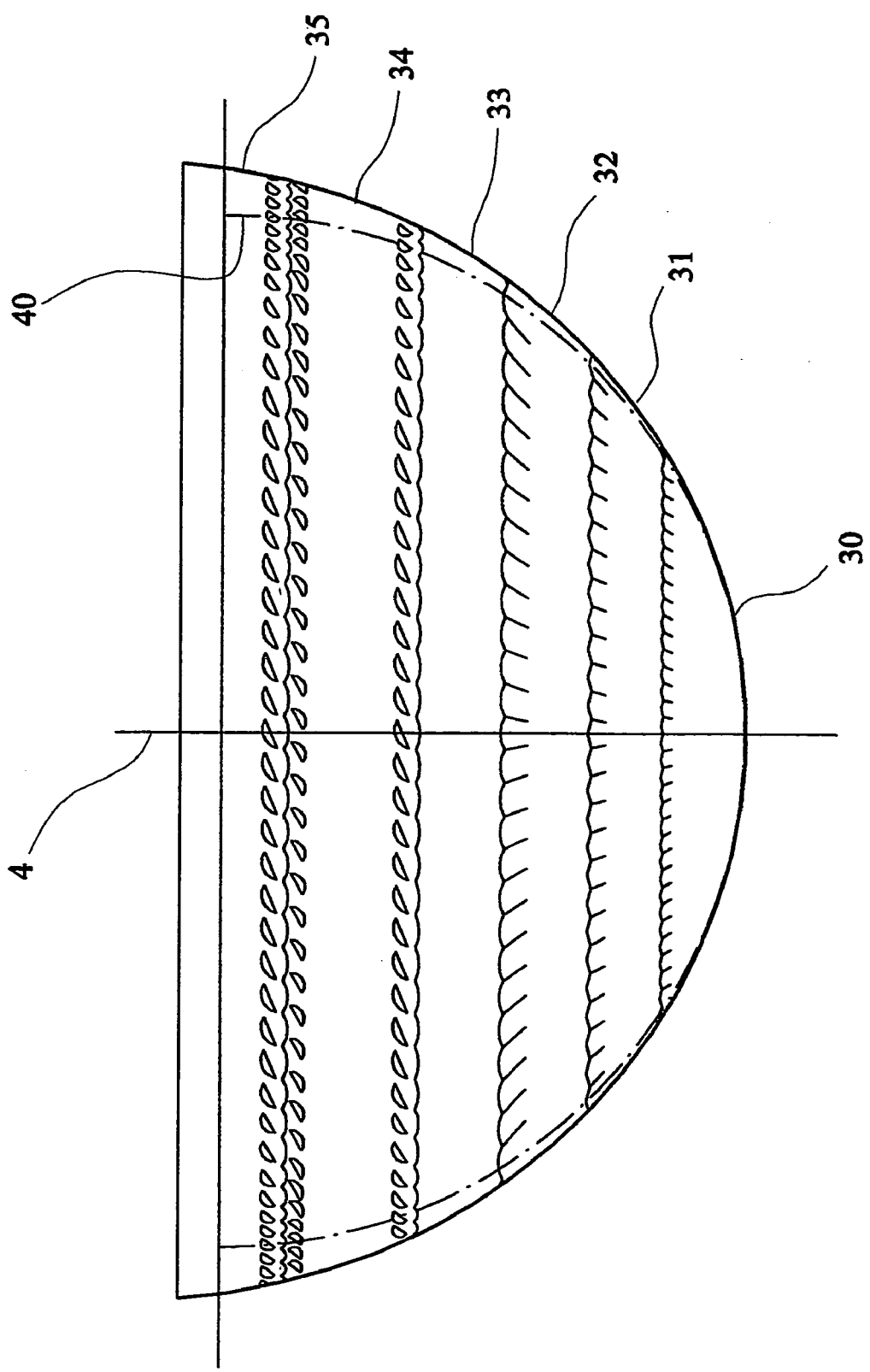
FIG. 3 is a side view of a hollow cup component of an orthopaedic joint prosthesis produced using the method of the present invention.

FIG. 3 shows the shape of the resulting cup component as depicted by the computer modelling software, arranged in the drawing with the axis of symmetry 4 vertical. The interfaces between the sphere portions 30 to 35 are depicted by shaded boundary lines. The lines are shaded rather than sharp because the modelling software is unable to identify a clear interface line at which the radius of curvature changes. For the purposes of comparison, the drawing shows in dotted outline 40 the outline of the cup component with a constant radius of 14 mm. The gap between the dotted outline 40 and the surface of the sphere portions 35 at the equator represents the deviation from sphericity which is available using the method of the present invention. In this example, the deviation from sphericity amounts to a difference in radius of over 1.0 mm at the equator. In practice, smaller deviations will enable the advantages of the present invention to be obtained, for example a difference in radius at the equator of not more than 0.5 mm, preferably not more than about 0.2 mm.

The invention claimed is:

1. A method of making a component of an orthopaedic joint prosthesis which has a bearing surface whose shape corresponds approximately to a part of a sphere and is symmetrical about its polar axis, the method making use of a cutting tool which has a circular cutting edge and which can be rotated about an axis which is perpendicular to the plane containing said cutting edge, and comprising the steps of:
 a. rotating the component about its polar axis and rotating the cutting tool about its axis, with the cutting edge of the cutting tool in contact with the surface of the component, to cut the surface in a region between the equator and the polar region of the component, and
 b. moving the cutting tool (i) in a direction parallel to the polar axis of the component while leaving the angle between the axis of the cutting tool and the polar axis of the component unchanged, and (ii) along its axis, and
 c. repeating step (a),
 the movements (i) and (ii) of the cutting tool causing the radius of curvature of the bearing surface to change continuously and monotonically as the angle between the radius and the polar axis of the component changes in the region between the equator and the polar region of the component, so that the shape of the bearing surface deviates from that of a true sphere in such a way that discontinuities in the shape of the bearing surface as a result of individual movements are minimised.

2. A method as claimed in claim 1, in which the cutting tool is moved along its axis in a direction towards the bearing surface of the component, as the cutting tool is moved along the polar axis in a direction away from the bearing surface of the component.

3. A method as claimed in claim 1, in which the bearing surface of the component is concave.

4. A method as claimed in claim 1, in which the bearing surface of the component is convex, and in which the cutting tool is annular so that the component has a circular cutting edge which can be applied against the convex bearing surface.

5. A method as claimed in claim 1, in which the simultaneous movements of the cutting tool along its axis, and in a direction parallel to the polar axis of the component, are performed in incremental steps.

6. A method as claimed in claim 5, in which the portion of the bearing surface which is defined by the cutting tool between any pair of consecutive incremental movements thereof extends through an angle of arc, measured with reference to the centre of the sphere that is defined by the bearing surface, of at least about 1°.

7. A method as claimed in claim 5, in which the portion of the bearing surface which is defined by the cutting tool between any pair of consecutive incremental movements thereof extends through an angle of arc, measured with reference to the centre of the sphere that is defined by the bearing surface, of not more than about 20°.

8. A method as claimed in claim 1, in which the bearing surface of the finished component includes a portion at and around the pole over which the radius of curvature is approximately constant.

9. A method as claimed in claim 8, in which the portion of the bearing surface over which the radius of curvature is approximately constant extends over a cone half angle, measured with reference to the centre of the sphere that is defined by the bearing surface, of at least about 10°.

10. A method as claimed in claim 1, which includes the step of sterilising the component so that the component is suitable for implantation in a human or animal body as a component of an orthopaedic joint prosthesis.

11. A method as claimed in claim 1, in which the bearing surface is on a cup component and the radius thereof decreases continuously and monotonically from the equator of the cup component towards the polar region thereof.

12. A method as claimed in claim 1, in which the bearing surface is on a head component and the radius thereof increases continuously and monotonically from the equator of the head component towards the polar region thereof.

* * * * *